US012611486B2

(12) United States Patent
Roël et al.

(10) Patent No.: US 12,611,486 B2
(45) Date of Patent: Apr. 28, 2026

(54) METHODS FOR PRODUCING TRANSPLANTABLE CARTILAGE TISSUE

(71) Applicant: CO.DON GmbH, Leipzig (DE)

(72) Inventors: Giulietta Roël, Berlin (DE); Christian Kaps, Berlin (DE); Claudia Eschen, Berlin (DE)

(73) Assignee: CO.DON GmbH, Leipzig (DE)

( * ) Notice: Subject to any disclaimer, the term of this patent is extended or adjusted under 35 U.S.C. 154(b) by 707 days.

(21) Appl. No.: 16/625,937

(22) PCT Filed: Jun. 22, 2018

(86) PCT No.: PCT/EP2018/066819
§ 371 (c)(1),
(2) Date: Dec. 23, 2019

(87) PCT Pub. No.: WO2019/002148
PCT Pub. Date: Jan. 3, 2019

(65) Prior Publication Data
US 2020/0147269 A1 May 14, 2020

(30) Foreign Application Priority Data
Jun. 25, 2017 (EP) .................................... 17177756

(51) Int. Cl.
| | |
|---|---|
| *C12Q 1/686* | (2018.01) |
| *A61L 27/38* | (2006.01) |
| *C12N 5/077* | (2010.01) |

(52) U.S. Cl.
CPC ........ *A61L 27/3817* (2013.01); *C12N 5/0655* (2013.01); *C12Q 1/686* (2013.01); *A61L 2430/06* (2013.01)

(58) Field of Classification Search
CPC ............. A61L 27/3817; A61L 2430/06; A61L 27/3852; C12N 5/0655; C12N 2513/00; C12Q 1/686; G01N 33/6887
See application file for complete search history.

(56) References Cited

U.S. PATENT DOCUMENTS

| | | | |
|---|---|---|---|
| 7,887,843 B2 | 2/2011 | Libera et al. | |
| 2003/0153078 A1 | 8/2003 | Libera et al. | |
| 2009/0176304 A1 | 7/2009 | Smith et al. | |
| 2010/0028308 A1 | 2/2010 | Knipper et al. | |
| 2011/0020798 A1 | 1/2011 | Holtzman et al. | |
| 2014/0178994 A1 | 6/2014 | West et al. | |
| 2014/0234964 A1* | 8/2014 | West .................... | C12N 5/0655 435/377 |
| 2015/0344847 A1 | 12/2015 | Malinin | |

FOREIGN PATENT DOCUMENTS

| | | | | |
|---|---|---|---|---|
| CN | 1661010 | A | 8/2005 | |
| CN | 101056974 | A | 10/2007 | |
| CN | 101317089 | A | 12/2008 | |
| CN | 101616693 | A | 12/2009 | |
| CN | 101657536 | A | 2/2010 | |
| CN | 101680881 | A | 3/2010 | |
| CN | 103223194 | A | 7/2013 | |
| CN | 103881969 | A | 6/2014 | |
| CN | 103987855 | A | 8/2014 | |
| CN | 105209607 | A | 12/2015 | |
| CN | 106834223 | A | 6/2017 | |
| CN | 109152864 | A | 1/2019 | |
| CN | 111032859 | A | 4/2020 | |
| DE | 10013223 | A1 | 10/2001 | |
| DE | 102009025347 | A1 | 12/2010 | |
| EP | 2390346 | A1 * | 11/2011 | .......... C12Q 1/6881 |
| EP | 2345450 | B1 | 9/2016 | |
| WO | 2004028339 | A2 | 4/2004 | |
| WO | 2005095585 | A1 | 10/2005 | |
| WO | 2011025367 | A1 | 3/2011 | |
| WO | 2013010045 | A1 | 1/2013 | |
| WO | 2019002148 | A1 | 1/2019 | |
| WO | 2020240040 | A1 | 12/2020 | |
| WO | 2016099453 | A1 | 6/2023 | |

OTHER PUBLICATIONS

Bartz et al. "An ex vivo human cartilage repair model to evaluate the potency of a cartilage cell transplant" J Transl Med (2016) 14: 317 (Year: 2016).*
Kieslinger et al. "EBF2 Regulates Osteoblast-Dependent Differentiation of Osteoclasts" Developmental Cell, vol. 9, 757-767, Dec. 2005. (Year: 2005).*
Wikipedia Reference Genes (Year: 2024).*
Ito "Evaluation of reference genes for human chondrocytes cultured in several different thermal environments" Int J. Hyperthermia, 2014; 30(3): 210-216 (Year: 2014).*
Christoph Bartz et al., "An ex vivo human cartilage repair model to evaluate the potency of a cartilage cell transplant", Journal of Translational Medicine, vol. 14, No. 1, Nov. 15, 2016, pp. 1-15.
Junjie Zhou et al., "Bone morphogenetic protein-7 promotes chondrogenesis in human amniotic epithelial cells", International Orthopaedics, Springer Berlin, DE, vol. 35, No. 6, Aug. 29, 2010, pp. 941-948.
Inigo Martinez et al., "Redifferentiation of In Vitro Expanded Adult Articular Chondrocytes by Combining the Hanging-Drop Cultivation Method With Hypoxic Environment", Cell Transplantation, vol. 17, No. 8, 2008, pp. 987-996.
Kristi L. Bennett et al., "HPV status-independent association of alcohol and tobacco exposure or prior radiation therapy with promoter methylation of FUSSEL18, EBF3, IRX1, and SEPT9, but not SLC5A8, in head and neck squamous cell carcinomas", Genes Chromosomes & Cancer., vol. 49, 2010, pp. 319-326.

(Continued)

*Primary Examiner* — Tracy Vivlemore
*Assistant Examiner* — Lauren K Van Buren
(74) *Attorney, Agent, or Firm* — Morse, Barnes-Brown & Pendleton, P.C.; Martin Z. Zhang; Russell L. Widom

(57) ABSTRACT

The present invention relates to a method for producing cartilage tissue by selecting and choosing from chondrocytes or spheroids, and use thereof as pharmaceutical composition, medicinal product or transplant. In particular, the invention relates to markers for identifying suitable chondrocytes for producing cartilage tissue, in particular for the purpose of transplantation.

8 Claims, No Drawings

(56)  References Cited

OTHER PUBLICATIONS

Anderer, et al., "In Vitro Engineering of Human Autogneous Cartilage," Journal of Bone and Mineral Research, 7(8):1420-1429, (Aug. 1, 2002).

Bin et al., "Cell surface markers during chondrogenic indution of mesenchumal stem cells derived from mouse hair follicle in vitro," Chinese Journal of Tissue Engineering Research, 16(32):5973-5977, (Aug. 5, 2012).

El-Magd, et al., "Bmp4 regulates chick Ebf2 and Ebf3 gene expression in somite development," Development, Growth & Differentiation, 55:710-722, (2013).

Feng et al., Differential expression gene of rat bone marrow mesenchumal stem cells and chondrocytes screened by gene chip technique, Journal of Clinical Rehabilitative Tissue Engineering Research, vol. 12, No. 10, Mar. 5, 2009.

International Preliminary Report on Patentability for PCT Application No. PCT/EP2020/065137, dated Sep. 23, 2021.

International Search Report for PCT Application No. PCT/EP2020/065137, dated Sep. 25, 2020.

Iwai et al., "Ex vivo cartilage defect model for the evaluation of cartilage regeneration using mesenchymal stem cells", Journal of Bioscience and Engineering, 11:357-364, (2010).

Ng, et al., "Extracellular matrix components and culture regimen selectively regulate cartilage formation by self-assembling human mesenchymal stem cells in vitro and in vivo," Stem Cell Research & Therapy, 7(183):1-12, (2016).

Pfaffl, "A new mathematical model for relative quantification in real-time RT-PCR," Nucleic Acids Research, 29 (9):2002-2007, (2001).

Roos et al., "The Knee injury and Osteoarthritis Outcome Score (KOOS): from joint injury to osteoarthritis," Health and Quality of Life Outcomes, 1:1-8, (Nov. 3, 2003).

Becher et al., "Safety of three different product doses in autologous chondrocyte implantation: results of a prospective, randomised controlled trial", Journal of Orthopedic Surgery and Research, 12: 71, (2017).

Dehne et al., "Chondrogenic Differentiation potential of osteoarthritic chondrocytes and their possible US in matrix-associated autologous chrondrocyte trasnplatnatio," Artrhitis Research and Therapy, Biomed Central. 11(5):R133, (2009).

Huang et al., "Cell-based tissue engineering strategies used in the clinical repair of articular cartilage," Biomaterials, 98:3-5 (2016).

Kawaki et al., "Cooperative Regulation of Chondrocyte Differentiation by CCN2 and CCN3 Shown by a Comprehensive Analysis of the CCN Family Proteins in Cartilage", Journal of Bone and Mineral Research, 23(11):1751-1764 (2008).

Kuroda et al., "Studies on cartilage cells in vitro - II. Changes in appregation and in cartilage-forming activity of cells maintained in monolayer cutlures". Experiemental Cell Research, 35(2):337-348, (1964).

Martin et al., "In vitro development of personalized cartilage microtissues uncovers an individualized differentiation capacity of human chondrocytes," Experiental Biology Medicine, 242(18): 1746-1756, (2017).

Murphy et al., "Engineering a fibrocartilage spectrum through modulation of aggregate redifferentiation," Cell Translant, 24(2): 235-245, (2015).

Niemeyer et al. "A Prospective, Randomized, Open-Label, Multicenter, Phase III Noninferioirity Trial to Compare the Clinical Efficacy of Matrix-Associated Autologous Chrondrocyte Implantation with Spheroid Technology Versus Arthroscopic Microfracture for Cartilage Defects of the Knee", Orthopaedic Journal of Sports Medicine, 7(7):1-11, (2019).

Non-Final Office Action issued in U.S. Appl. No. 17/615,278 dated Apr. 23, 2025.

Schubert et al., "Long-term effects of chondrospheres on cartilage lesions in an autologous chondrocyte implantation model as investigated in the SCID mouse model," International Journal of Molecular Medicine, 23:456 (2009).

Vapniarsky et al., "Tissue engineering toward temporomandibular joint disc regeneration," Sci Transl Med., 10(446): 1-28, (2018).

Wang et al., "Advance in autologous chondrocyte implantation for repair of articular cartilage injury," Orthopedic Journal of China, 23(4):328-331, (2015).

Chua et al., "Insulin-Transferrin-Selenium Prevent Human Chondrocyte Dedifferntiation and Promote the Formation of High Quality Tissue Engineering Human Hyaline Cartilage", European Cells and Materials, 9: 58-67, (2005).

Suzuki et al., "The metabolism of hyaluronan in cultured rabbit growth plate chondrocytes during differentiation", Biochimica et Biophysica Acta, 1743: 57-63, (2005).

Zipper et al., "Development of chick limb bud chondrocutes in cell culture: Morphologic and oxidative metabolic observations", Clin Orthop Relat Res., 155: 186-195, (1981).

Chi Guang-fan et al., "Experimental study of repair of articular cartilage full-thickness defect by tissue engineered autograft", Chin J End, 23(6): 516-519 (2004).

Yang et al., Journal of Practical Orthopaedics, 21(1): 59-61, (2015).

Examiner's Report issued in Canadian application No. 3,067,770 dated Aug. 22, 2025.

Examiner's Report issued in Canadian application No. 3141639 dated Aug. 1, 2025.

Final Office Action issued in U.S. Appl. No. 17/615,287 dated Nov. 4, 2025.

Office action and search report issued in Eurasian application No. 202591404 dated Sep. 8, 2025.

Office action issued by Korean Patent Office for Korean patent application No. 1020217043019 Sep. 30, 2025.

* cited by examiner

METHODS FOR PRODUCING TRANSPLANTABLE CARTILAGE TISSUE

CROSS-REFERENCE TO RELATED APPLICATIONS

This application is a U.S. National Phase of International Patent Application No. PCT/EP2018/066819, filed Jun. 22, 2018, which claims priority to European Patent Application No. 17177756.8, filed Jun. 25, 2017, all of which are herein incorporated by reference in their entireties.

The present invention relates to a method for producing cartilage tissue by selecting and choosing from chondrocytes or spheroids, and to the use thereof as pharmaceutical composition, medicament or transplant material. In particular, the invention relates to markers for identifying suitable chondrocytes for the production of cartilage tissue, in particular for the purpose of transplantation.

Although articular cartilage demonstrates notable resilience, this tissue is unable or is hardly able to repair or regenerate itself, and untreated legions may lead to osteoarthritis. This low potential for spontaneous regeneration has led to the development of cell therapies, such as autologous chondrocyte transplantation (ACT), with the aim of providing a functional and pain-free repair of articular cartilage defects. There is a great need for methods for cartilage regeneration, for example in young active patients with traumatic lesions or even with symptoms of cartilage degeneration, and for treatment of cartilage defects.

Biochemical and molecular studies with human chondrocytes have been hindered by a series of factors, such as the lack of availability of human tissue in conjunction with the very small number of cells available in a biopsy, the limited proliferation capacity and the high phenotypic instability of cultivated chondrocytes.

A chondrocyte (cartilage cell) is a cell that originates from chondroblasts and that is established in the cartilage tissue. Together with the intercellular substances (extra cellular matrix (ECM)), the chondrocytes form the primary components of cartilage, in particular articular cartilage.

It is already known, by mimicry of certain processes of embryonal development, for example to cultivate human cartilage cells three-dimensionally on an agarose substrate, such that cell aggregates are produced which are superior to the monolayer cells in terms of their differentiation ability and which for example have cartilage-like properties. These properties, which reflect the native articular cartilage tissue as accurately as possible, are characterised by the expression of collagen II (primary structural protein in the extracellular matrix of hyaline cartilage), of proteoglycans, for example aggrecan, and the intracellular chondrocyte-specific protein S100.

In addition, it is desirable for the expression of collagen I, which is necessarily up-regulated during the cell multiplication phase in the monolayer culture, to be reduced again in the cell aggregates, since this protein is practically absent in native articular cartilage. The cell aggregates thus generated (spheroids) have been offered since 2002 by the applicant in order to treat cartilage defects, caused by injury, in younger patients. To this end, native articular cartilage tissue is removed from the patient and a biopsy of hyaline cartilage is removed from a healthy cartilage area. By enzymatic digestion of the cartilage tissue by means of a collagenase solution, the cartilage cells (chondrocytes) located in the cartilage tissue are isolated and are multiplied by means of standard cell culture conditions in cell culture flasks (monolayer culture) in the presence of autologous serum, and sufficient chondrocytes are provided for the production of transplantable cartilage tissue. The multiplied cells form cell aggregates, or what are known as spheroids, which may be transplanted. However, the cell aggregates produced in this way are limited in respect of their differentiation status and usually demonstrate a relatively weak local expression of the important substance collagen II and a marginal synthesis of proteoglycans with relatively strong expression of the undesired substance collagen I. In order to improve the differentiation of these cell aggregates further, it is possible to enrich the culture medium with certain bioactive substances. These include primarily the growth factors TGF-β1-3 and ascorbic acid (vitamin C) described in many instances in the literature as cofactor for collagen synthesis. However, this biochemical stimulation on the one hand is often insufficient to induce the differentiation of the cartilage cells in the 3D cell aggregate to an extent that cartilage-typical constructs are produced, and on the other hand the use of growth factors such as TGF-β is disputed in particular for clinical use in humans.

The cultivation of human cells in the form of three-dimensional cell aggregates, for example in the form of what are known spheroids, is already described for clinical use in humans, for example as autologous cartilage transplant, in DE 100 13 223, which concerns a method for the in vitro production of three-dimensional cartilage tissue and bone tissue from bone stem cells, cartilage stem cells or mesenchymal stem cells. Here, the cells are firstly cultivated in a monolayer culture and are then cultivated in suspension until a cell aggregate is produced that contains at least 40 vol % extracellular matrix, in which differentiated cells are embedded.

In the method, cell aggregates are produced by cultivating cells for at least 1-2 weeks in cell culture vessels coated with agarose.

U.S. Pat. No. 7,887,843 B2 discloses a method for the in vitro production of three-dimensional cartilage tissue and bone tissue, wherein transplantable spheroids are produced from bone stem cells, cartilage stem cells or mesenchymal stem cells by cultivating $1 \times 10^5$ cells for at least two weeks.

Anderer et al. (Journal of Bone and Mineral Research (2002), New York, NY, US, Vol. 17, no. 8, p. 1420-1429) also discloses a method for the in vitro production of three-dimensional cartilage tissue. In accordance with this method $1 \times 10^5$ or $2 \times 10^5$ chondrocytes are cultivated for 5 days, 2 weeks, 1, 2 and 3 months in order to produce spheroids.

The cartilage tissues produced in vitro described in the prior art do not present any expression patterns of essential matrix proteins, such as collagen type II, that are similar to those of native tissues. Rather, the composition of the extracellular matrix (ECM) produced in vitro from the chondrocytes deviates significantly from native cartilage tissue. However, the composition of the ECM is key for the biological functionality of the cartilage, for example the mechanical load-bearing capacity. There is therefore a need for new techniques for producing cartilage tissue and also for quality control.

"Transplantable cartilage tissue" means the production ex-vivo or with the aid of an in-vitro technique, wherein the produced tissue corresponds largely to the native tissue or is identical to the native tissue. In the sense of the invention the transplantable cartilage tissue corresponds largely to the native tissue for example in relation to the expression or expression pattern of the extracellular matrix, for example in relation to the expression or expression pattern of structural proteins or proteids such as type II collagen and/or S100 protein and/or the tissue-specific proteoglycans, for example cartilage-specific proteoglycans, such as aggrecan. The expression or expression pattern can be detected for example histologically or immunohistologically.

The tissue from which the chondrocytes are isolated is selected for example from musculoskeletal tissue, skeletal tissue, cartilage, bone, meniscus, intervertebral disc, bone marrow, joints or tendons. The transplantable cartilage tissue produced by the method according to the invention is similar to the native tissue in respect of the composition and protein expression (see above).

Native articular cartilage tissue has a composition of the extracellular matrix formed of approximately 60 to 80% water in relation to the wet weight of the articular tissue. The high water content is important for the mechanical load-bearing ability of the cartilage tissue and, together with the proteoglycans, is important for the "sponge effect". Besides water, native articular cartilage contains the structural proteins or proteins of the matrix. Here, the structural macro-molecules account for approximately 20 to 40% of the wet weight of the articular cartilage tissue.

In the case of native articular cartilage tissue, the collagen proportion is 60%, the proteoglycan proportion is 25 to 35%, and the non-collagen protein and glycoprotein proportion is 15 to 20% in relation to the cartilage dry weight. Collagen type II accounts for approximately 90 to 95% of the total collagen content of the native articular cartilage tissue.

Native human articular cartilage tissue contains approximately 1 to 5% cartilage cells (chondrocytes) in relation to the tissue volume. Here, the cartilage cells are the essential producers of the matrix molecules of the functional native tissue.

There is thus a great need to provide chondrocytes which have a sufficient quality and can produce a suitable transplantable cartilage tissue which corresponds to the native tissue, such that success of the treatment can be expected. This treatment success is largely dependent on the quality of the transplantable cartilage tissue.

The object of the invention is therefore to provide an improved transplantable cartilage tissue, in particular having improved properties, in particular sufficient quality, such as identity with native chondrocytes and spheroids of improved quality such that high-quality transplants can be obtained, in particular for the successful treatment and therapy of articular cartilage defects.

The inventors were surprisingly able to identify markers in isolated chondrocytes which allow a sufficient quality for the production of transplantable cartilage tissue. The markers according to the invention allow in particular the determination of cartilage cell identity ("identity markers") of the isolated chondrocytes in a culture to the native chondrocytes.

A suitable cartilage cell identity in turn allows the production of suitable transplantable cartilage tissue, since on the one hand a sufficient cartilage-specific extracellular matrix (ECM) can be achieved, and on the other hand an improved treatment of articular cartilage defects is achieved.

In a further embodiment the markers according to the invention allow the determination of the purity or impurity of the isolated chondrocytes or spheroids ("purity markers").

The aforementioned markers ensure a sufficient quality and therefore constitute "quality markers".

The invention therefore relates to a method for the selection of chondrocytes or spheroids for the production of transplantable cartilage tissue, wherein at least one quality marker or identity marker or purity marker is determined.

The method according to the invention for the selection of chondrocytes or spheroids for the production of transplantable cartilage tissue comprises, in a first step, that the chondrocytes are multiplied in a monolayer culture (see above, what is known as two-dimensional expansion culture), and, in a second step, can aggregate to form spheroids (see above, what is known as 3D cultivation), such that the chondrocytes aggregate to form spheroids, and spheroids may be selected.

In a preferred embodiment the quality marker or identity marker or purity marker is selected from the group KAL1, CRTAC1, NRN1 or EBF3, which is (are) determined in vitro.

In a preferred embodiment the quality markers or identity markers are selected from the group KAL1, CRTAC1, and/or the purity markers are EBF3, NRN1. In particular synoviocytes are disadvantageous impurities which may be determined in vitro by the purity marker EBF3. Such impurities may reduce the quality of the chondrocytes and also spheroids.

In a further preferred embodiment what is known as a potential marker may be sought in accordance with the invention in addition to the aforesaid markers, which potential marker allows a prediction of the activity and regeneration capability of the transplantable cartilage tissue to be obtained from the spheroids. Such potential markers according to the invention are preferably proteoglycans, particularly preferably aggrecan (ACAN).

TABLE 1

| | | Marker genes according to the invention | |
|---|---|---|---|
| Marker | Accession Nr. | Name | Functions in the quality testing and selection |
| CRTAC1 | NM_018058 | Homo sapiens cartilage acidic protein 1 (CRTAC1). transcript variant 1. mRNA | Chondrogenic identity marker for spheroids |
| NRN1 | NM_001278710 | Homo sapiens neuritin 1 (NRN1). transcript variant 2. mRNA | Chondrogenic purity marker for spheroids |
| KAL1 (ANOS1) | NM_000216 | Homo sapiens anosmin 1 (ANOS1). mRNA | Chondrogenic identity marker for monolayer culture |
| EBF3 | NM_001005463 | Homo sapiens early B-cell factor 3 (EBF3). mRNA | Chondrogenic purity marker for spheroids |
| ACAN | NM_001135 | Homo sapiens aggrecan (ACAN). transcript variant 1. mRNA | Potential marker for spheroids |

The associated DNA sequences can be clearly identified by the accession no. (for example NCBI).

The in vitro determination of the markers according to the invention is preferably achieved by determining the gene expression of these markers and also the level of the gene expression in the isolated chondrocytes and obtained spheroids, which for example can be determined routinely by the polymerase chain reaction (PCR, in particular qPCR); see the examples.

In accordance with the invention the markers show gene expression as well as increased or reduced gene expression in the method according to the invention, thus demonstrating their suitability as markers.

In a further embodiment the gene expression or gene expression level may also be determined in the presence of, and in comparison to, reference genes and gene expression or gene expression level thereof. This allows a normalisation of the gene expression and quantification thereof, also by means of software support; see Michael W. Pfaffl, A new mathematical model for relative quantification in real-time RT-PCR, Nucleic Acids Research, 2001, Vol. 29, No. 9.

TABLE 2

Reference genes according to the invention

| Reference gene | Accession Nr. | Name | Functions in the quality testing and selection |
|---|---|---|---|
| B2M | NM_004048 | Homo sapiens beta-2-microglobulin (B2M). mRNA | Reference gene |
| TOP1 | NM_003286 | Homo sapiens topoisomerase (DNA) I (TOP1). mRNA | Reference gene |

The associated DNA sequences can be clearly identified by the accession no. (for example NCBI).

Within the scope of this invention the term "selection" means that, for example, chondrocytes or spheroids that have no gene expression of the markers according to the invention or that have a relatively low gene expression or gene expression level compared to other chondrocytes or spheroids are discarded. A person skilled in the art is capable of distinguishing between a stronger gene expression and a weaker gene expression for one or more chondrocytes/spheroids on the basis of the obtained gene expression patterns, and of choosing such chondrocytes/spheroids accordingly.

In a further preferred embodiment, after multiplication, isolated chondrocytes and spheroids obtained therefrom which have the following ratios of gene expression to one/both reference genes (R), more specifically B2M and/or TOP1, shall be selected and chosen:

| | |
|---|---|
| CRTAC1/R | >0.003 |
| NRN1/R | ≥0.1 |
| KAL1/R | >1.0 |
| EBF3/R | ≤0.4 |
| ACAN/R | ≥0.29 |

Further preferred ratios are

| | |
|---|---|
| CRTAC1/R | ≥0.006, in particular ≥0.009 and ≥0.012 |
| NRN1/R | ≥0.2, in particular ≥0.3 and ≥0.4 |
| KAL1/R | ≥2.0, in particular ≥3.0 and ≥4.0 |
| EBF3/R | ≤0.3, in particular ≤0.2 and ≤0.1 |
| ACAN/R | ≥0.39, in particular ≥0.49 and ≥0.59 |

The stated values are understood to be suitable threshold values.

The invention therefore relates to a method for selecting chondrocytes or spheroids for the production of transplantable cartilage tissue, wherein the markers according to the invention are determined in comparison to a reference gene.

In a further preferred embodiment, during the course of the performed determinations of the purity marker EBF3, the proportion of synoviocytes as impurity in the isolated chondrocytes after multiplication or in the obtained spheroids in relation to the total number of cells is less than or equal to 9%, in particular less than or equal to 5%.

The method according to the invention allows the selection of chondrocytes and spheroids that are chosen specifically for a cartilage tissue to be transplanted. This is based on the particular properties of the markers according to the invention, specifically quality marker or identity marker or purity marker. Consequently, chondrocytes and spheroids which have a specific gene expression are chosen, and corresponding gene products can be detected for example by means of PCR.

The invention therefore relates to isolated chondrocytes or isolated obtained spheroids, obtainable by a method according to the invention. Also comprised is a transplantable cartilage tissue, in particular in the form of a drug or medicinal product or in the form of a pharmaceutical composition containing such chondrocytes or spheroids, in particular for use in the treatment of articular cartilage defects and/or autologous chondrocyte transplantation.

In a further preferred embodiment of the invention the transplantable cartilage tissue according to the invention is administered to a patient with the aid of an applicator (see EP2345450B1 (co.fix 150 of the applicant) or DE102009025347A1). The transplanted cartilage tissue may preferably be kept in the form of a pharmaceutical composition in a physiological saline solution together with further auxiliaries and additives.

The following drawings and examples serve to explain the invention, but without limiting the drawings and examples.

EXAMPLE 1

Isolation of Cartilage Cells (Chondrocytes) from Cartilage Biopsy and Cell Cultivation
Cartilage-Specific Cells Cartilage-specific cells (chondrocytes) were isolated from a cartilage biopsy by means of enzymatic digestion using collagenase (350 units/ml). The enzymatic digestion lasted between 4 and 6 hours and took place at 37° C. The cartilage biopsy was taken from femur condyles of the knee joint. After the enzymatic digestion, the chondrocytes were centrifuged, washed, counted and sown in tissue culture flasks together with cell culture medium (Alpha MEM/Ham's F12 1:1, 1% glutamine) and autologous serum (10-15% human serum). For expansion, the cells were cultured in vitro for between 7 and 38 days at 37° C. in the two-dimensional expansion culture (monolayer). The cell culture medium was replaced every 3-6 days. If the cell cultures were confluent, the cell culture was passaged with the aid of papain and divided between a number of culture flasks.

After reaching a sufficient number of cells from the monolayer culture, 200,000 cells were sown per well in microtiter plates coated with 2% agarose. The cells aggregated and formed a three-dimensional, round structure (spheroid). During the cultivation of the spheroids, the cell culture medium (Alpha MEM/Ham's F12 1:1; 1% glutamine), which was mixed with 10% autologous serum, was replaced regularly (every 3-6 days). The 3D cultivation lasted for between 14 and 42 days.

After the spheroid cultivation, the cartilage cell transplant was prepared for transport and implantation by collecting the spheroids in the medical product carrier (0.9% NaCl) and then transferring them to the applicator system co.fix 150 or a syringe.

To summarise, the production of cartilage cell transplants consisted of a monolayer cultivation phase so as to multiply the isolated chondrocytes, and of a 3D cultivation phase so as to aggregate the chondrocytes to form spheroids. The cartilage cell transplant was intended for autologous application, that is to say was intended for implantation in the knee of the same patient.

EXAMPLE 2 a.) RNA Isolation

The cartilage cells were cultivated in a two-dimensional expansion culture (monolayer) up to production of the spheroids and were then removed from the bottom of the cell culture flask and from the cell complex with the aid of an enzyme solution (papain). $1\times10E6$ of these cartilage cells were removed from the cell suspension for the identity test and were transferred into a reaction vessel, whereas the rest of the cells were used for the subsequent production of the spheroids. The monolayer cells relevant to the test were centrifuged off and the cell pellet was lysed in the appropriate lysis buffer (PeqGOLD, Peqlab), shock-frozen, and stored at $-70°$ C. until RNA isolation. For marker testing on cartilage cell spheroids, 8 spheroids were removed from the well plate after two weeks of culture time, were washed with PBS, and were lysed with the appropriate lysis buffer (PeqGOLD, Peqlab). The spheroids received in the lysis buffer were mechanically homogenised by syringe and cannula for optimal cell breakdown by being drawn off and expelled back out. The lysate was then shock-frozen in liquid nitrogen and stored at $-70°$ C. until RNA isolation.

The extraction of the total RNA from the cartilage cell spheroids and monolayer cells was performed on the basis of the peqGOLD Total RNA Kit from Peqlab or using the RNeasy Plus Mini Kit from Qiagen in accordance with the manufacturer's instructions. The isolated RNA was eluted in nuclease-free water and stored at $-70°$ C. until cDNA synthesis. After the RNA isolation, the quantity, quality and integrity of the RNA was determined using a spectrophotometer (NanoDrop, Thermo Scientific) and by means of a bioanalyzer (Agilent) in accordance with the manufacturer's instructions.

b.) cDNA Synthesis cDNA synthesis was performed on the basis of the Transcriptor First Strand cDNA Synthesis Kit (Roche) in accordance with the manufacturer's instructions. For each sample, 80 ng of total RNA were transcribed with use of the random Hexamer primer. The template-primer mix was placed in a sterile reactor vessel for a reaction volume of 20 μl. The following further components were pipetted to the template-primer mix: Transcriptor Reverse Transcriptase Reaction Buffer, Protector RNase Inhibitor, Deoxynucleotide Mix, Transcriptor Reverse Transcriptase. The reaction batches were mixed, centrifuged together, and then incubated in a thermocycler. The reverse-transcribed cDNA was then diluted with nuclease-free water to a final concentration of 1 ng/μl. The samples were stored at $-20°$ C. until their further use in the qPCR analyses.

c.) qPCR

For the qPCR analyses, the qPCT technique with the LightCycler® 480 Instrument II (Roche) in 384-well format was used. The primers were HPLC-purified and were dissolved in nuclease-free water to a concentration of 10 μM. The samples were used in a concentration of 10 μM. For the markers to be measured, previously defined qPCR reaction conditions with regard to the primer and sample concentration and the use of additives were established. For all samples, a master mix was produced according to the reaction condition of the specific primer. 8 μl of the reaction mix specific for each target gene were pipetted into the corresponding well in the 384-well plate, and then 2 μl cDNA sample (1 ng/μl) were added, whereby a total volume of 10 μl was given for each qPCR reaction.

The qPCR analysis is based on the exponential increase of the fluorescence-labelled PCR amplification products of the gene of interest. The qPCR data were analysed with the aid of the LightCycler® 480 software with use of the Advanced Relative Quantification software module (Roche). The used detection format was the so-called Mono Colour Hydrolysis sample/URL Sample Program with the following parameters: excitation filter 483 nm, emission filter 533 nm, filter combination FAM. qPCR data were generated and analysed with the software modules for the relative quantification. Absolute qPCR data (CP values) of the various target genes were generated by the Abs Quant/2nd Derivative Max method. The Cp value (crossing point or cycle threshold) is the number of PCR cycles that are necessary to exceed a defined threshold value of the fluorescence signal. The fluorescence signal detection was performed at the end of each cycle at $72°$ C.

The normalisation of the mRNA expression level of the target gene relative to reference gene was performed with the aid of the so-called "efficiency" method with use of the Advanced Relative Quantification software module (Roche). Two reference genes, TOP1 and B2M, were each also measured as internal normalisation control for each sample. The expression of the target gene was normalised to this reference gene, and normalised data were provided automatically from the Software Module Advanced Relative Quantification as target/reference values (T/R). The mathematical model forming the basis of this software module is based on the relationship between the Cp values of the target gene in comparison to the reference genes and under consideration, inter alia, of the primer-specific amplification efficiency.

The normalised expression values were used for the testing of the quality of the cartilage cell transplant. Critical quality attributes were the identity, purity and potential, wherein at least one specific marker was identified for each quality parameter and could be measured in order to confirm sufficient quality. The normalised expression values of a marker had to satisfy the acceptance limits defined for the confirmation of sufficient quality. The value for the quality parameter was based on the mRNA expression level in the monolayer cartilage cells (KAL1) or spheroids (CRTAC1, NRN1, EBF3 and ACAN).

Table 3 shows the application of the described selection to cartilage transplant products. In total, 48 cartilage transplant products were produced as described and subjected to testing for identity, purity (impurity) and potential with the markers according to the invention. Of the 48 cartilage transplants, 48 satisfied the criteria of identity in the monolayer (KAL1) and in the spheroid (CRTAC1). Of the 48 cartilage transplants, 4 failed to satisfy the criterion of purity (impurity) (EBF3, NRN1), and 19 of the 48 cartilage transplants failed to satisfy the criterion of potential. On the whole, 22 of the 48 cartilage transplants failed to satisfy the criterion of cartilage cell quality (identity, purity/impurity or potential). 26 of the 48 cartilage cell transplants satisfied the criterion of cartilage cell quality (identity, purity/impurity or potential) and were suitable for the production of transplantable cartilage tissue and were chosen.

TABLE 3

| | | | | | | | Choice according to the stated threshold values | | | | | |
| patient ID | KAL1 mRNA levels (T/R) in ML cells >1.0 | CRTAC1 mRNA levels (T/R) in spheroids >0.003 | NRN1 mRNA levels (T/R) in spheroids >0.1 | EBF3 mRNA levels (T/R) in spheroids ≤0.4 | Amount of synoviocyte impurity in spheroids (%) ≤9% | ACAN mRNA levels (T/R) ≥0.29 | Passed acceptance limits yes/no |
|---|---|---|---|---|---|---|---|
| 2410 | 19.88 | 0.99 | 0.82 | 0.08 | 1.80 | 0.21 | no |
| 1312 | 25.97 | 2.54 | 1.42 | 0.08 | 1.70 | 0.44 | yes |
| 2601 | 15.07 | 1.02 | 0.94 | 0.07 | 1.50 | 0.35 | yes |
| 2277 | 16.17 | 0.44 | 0.93 | 0.05 | 1.00 | 0.29 | yes |
| 2417 | 52.17 | 1.20 | 2.46 | 0.07 | 1.60 | 1.45 | yes |
| 2418 | 40.96 | 0.54 | 1.54 | 0.19 | 4.30 | 0.98 | yes |
| 2420 | 13.80 | 0.92 | 1.46 | 0.04 | 0.80 | 0.81 | yes |
| 2424 | 3.48 | 3.14 | 1.18 | 0.04 | 0.90 | 0.23 | no |
| 2423 | 23.67 | 3.07 | 1.22 | 0.05 | 1.00 | 0.24 | no |
| 2294 | 152.60 | 0.50 | 0.87 | 0.07 | 1.60 | 2.22 | yes |
| 10540 | 18.20 | 0.88 | 1.80 | 0.08 | 1.68 | 0.89 | yes |
| 10541 | 9.10 | 0.52 | 1.38 | 0.05 | 1.03 | 0.96 | yes |
| 10542 | 18.00 | 0.60 | 0.86 | 0.02 | 0.36 | 0.25 | no |
| 10543 | 6.80 | 1.66 | 1.63 | 0.11 | 2.51 | 0.60 | yes |
| 10544 | 37.80 | 2.09 | 2.46 | 0.02 | 0.49 | 2.50 | yes |
| 10546 | 42.40 | 2.83 | 0.94 | 0.02 | 0.54 | 0.82 | yes |
| 10551 | 6.40 | 0.22 | 0.76 | 0.45 | 10.04 | 0.64 | no |
| 10552 | 7.50 | 0.38 | 1.84 | 0.02 | 0.49 | 0.04 | no |
| 10561 | 12.70 | 1.66 | 0.73 | 0.03 | 0.58 | 0.27 | no |
| 10562 | 6.70 | 1.94 | 2.01 | 0.01 | 0.11 | 0.22 | no |
| 10563 | 15.70 | 1.93 | 1.86 | 0.04 | 0.90 | 0.39 | yes |
| 10564 | 18.50 | 0.52 | 0.63 | 0.03 | 0.72 | 0.08 | no |
| 10566 | 49.10 | 2.24 | 2.40 | 0.04 | 0.78 | 1.34 | yes |
| 10567 | 2.40 | 0.95 | 0.57 | 0.02 | 0.54 | 0.19 | no |
| 10568 | 34.90 | 1.20 | 0.91 | 0.16 | 3.57 | 0.95 | yes |
| 10569 | 18.80 | 1.12 | 2.12 | 0.05 | 1.14 | 0.50 | yes |
| 10570 | 2.60 | 1.04 | 0.82 | 0.01 | 0.18 | 0.14 | no |
| 10571 | 23.90 | 0.80 | 1.58 | 0.01 | 0.27 | 0.87 | yes |
| 11637 | 32.90 | 0.35 | 1.31 | 0.18 | 3.94 | 4.86 | yes |
| 11638 | 1.30 | 0.08 | 0.63 | 0.60 | 13.37 | 0.35 | no |
| 11662 | 16.54 | 0.48 | 1.63 | 0.07 | 1.52 | 1.55 | yes |
| 11664 | 15.79 | 0.62 | 2.13 | 0.16 | 3.58 | 3.60 | yes |
| 11665 | 14.62 | 0.23 | 0.94 | 1.06 | 23.86 | 1.03 | no |
| 10025 | 3.32 | 0.55 | 0.41 | 0.28 | 6.21 | 0.31 | yes |
| 10049 | 31.12 | 0.13 | 1.61 | 0.06 | 1.28 | 1.18 | yes |
| 10058 | 4.94 | 0.25 | 0.39 | 0.08 | 1.86 | 0.06 | no |
| 10069 | 10.05 | 0.13 | 0.76 | 0.02 | 0.47 | 0.52 | yes |
| 10111 | 6.27 | 0.27 | 0.26 | 0.36 | 8.07 | 0.25 | no |
| 10112 | 1.01 | 0.86 | 0.21 | 1.44 | 32.29 | 0.04 | no |
| 10134 | n.d. | 0.18 | 0.1 | 0 | 0.00 | 0.29 | yes |
| 10138 | 5.25 | 0.86 | 0.52 | 0.15 | 3.41 | 0.07 | no |
| 10161 | 3.68 | 0.64 | 0.65 | 0.15 | 3.27 | 0.17 | no |
| 10162 | 1.79 | 0.84 | n.d. | 0.05 | 1.19 | 0.06 | no |
| 10187 | 1.41 | 0.37 | 0.65 | 0.07 | 1.50 | 0.24 | no |
| 10192 | 1.59 | 4.18 | 0.44 | 0.34 | 7.58 | 0.32 | yes |
| 10547 | 1.93 | 1.48 | 1.16 | 0.01 | 0.29 | 0.29 | yes |
| 10567 | 2.39 | 0.96 | 0.57 | 0.02 | 0.54 | 0.19 | no |
| 10570 | 2.57 | 1.04 | 0.82 | 0.01 | 0.18 | 0.14 | no | n.d.= not determined.
ID = identifier.
T/R = target to reference ratio.

EXAMPLE 3

Production of cartilage tissue to be transplanted by means of cartilage cells multiplied in monolayer culture of defined quality, in this case: identity A biopsy of hyaline cartilage was taken from a healthy cartilage area from a patient with cartilage defect to be treated. By enzymatic digestion of the cartilage tissue with a collagenase solution, the cartilage cells (chondrocytes) in the cartilage tissue were isolated and multiplied by means of standard cell culture conditions in cell culture flasks (mono-layer culture) in the presence of autologous serum, so that a maximum Population Doubling Level (PDL) of 10 was not exceeded and sufficient chondrocytes for production of transplantable cartilage tissue were available. A part of the cartilage cells multiplied in the monolayer were used to determine the cartilage cell identity, and the remaining part were used to produce transplantable cartilage tissue. The markers for cartilage cell identity in the monolayer culture revealed that cartilage cells were present in the cartilage cell culture. For cartilage cell identity in the monolayer culture, the total RNA of the chondrocytes cultivated in the mono-layer was isolated by means of conventional molecular biology techniques and was transcribed into cDNA by means of reverse transcriptase. The expression of at least one reference gene (above, Table 2) and of the identity marker "KAL1" was determined by means of conventional polymerase chain reaction. The expression of "KAL1" was set in relation to the expression of the reference gene and thus gave a normalised gene expression value for the identity marker "KAL1". The expression of "KAL1" indicated that chondrocytes of sufficient quality (identity) for the production of transplantable cartilage tissue were present.

In order to produce the transplantable cartilage tissue, at least 100,000 of the chondrocytes of sufficient quality (identity) multiplied in the monolayer were transferred into a cell culture vessel in the presence of standard cell culture media and autologous serum. The cell culture vessel prevented sticking of the chondrocytes, for example by means of an agarose coating of the cell culture bottom. After a few days, the chondrocytes attached to one another and formed aggregates, or what are known as spheroids. The spheroids were cultivated over a period of at least 1-2 weeks and formed a cartilage-like extracellular matrix (spheroid culture). This cartilage tissue (chondrocytes of sufficient quality (identity) and cartilage-like extracellular matrix) was suitable, after introduction into the cartilage defect of the patient to be treated, for building a replacement cartilage tissue which filled the defect and performed the function of the natural cartilage tissue.

Cartilage tissue of insufficient quality (identity in the monolayer culture) is not suitable for building replacement cartilage tissue and was discarded.

EXAMPLE 4

Production of cartilage tissue to be transplanted by means of cartilage cells in spheroid culture of defined quality, in this case: identity The cartilage cells isolated in Example 3 and multiplied in the monolayer were used for the production of transplantable cartilage tissue.

As described in Example 3, the chondrocytes multiplied in the monolayer were transferred into a special cell culture vessel which prevented sticking of the chondrocytes, so that, after a few days, aggregates or what are known as spheroids were formed. The spheroids were cultivated over a period of at least 1-2 weeks and formed a cartilage-like extracellular matrix (spheroid culture).

The marker for cartilage cell identity in the spheroid culture indicated that cartilage cells were present in the spheroid culture. In order to determine the cartilage cell identity in the spheroid culture, the total RNA of part of the chondrocytes cultivated in the spheroids was isolated by means of conventional molecular biology techniques and was transcribed into cDNA by means of reverse transcriptase. The expression of at least one reference gene (above, Table 2) and of the identity marker "CRTAC1" was determined by means of standard polymerase chain reaction (PCR). The expression of "CRTAC1" was set in relation to the expression of the reference gene and thus gave a normalised gene expression value for the identity marker "CRTAC1". The expression of "CRTAC1" revealed that chondrocytes of sufficient quality (identity) for transplantation of the cartilage tissue were present in the spheroid.

This cartilage tissue (chondrocytes of sufficient quality (identity) and cartilage-like extracellular matrix) was suitable, after introduction into the cartilage defect of the patient to be treated, for building a replacement cartilage tissue, which filled the defect and performed the function of the natural cartilage tissue. Cartilage tissue of insufficient quality (identity in the spheroid culture) is not suitable for building replacement cartilage tissue and was discarded.

EXAMPLE 5

Production of cartilage tissue to be transplanted by means of cartilage cells in spheroid culture of defined quality, in this case: purity The cartilage cells isolated in example 3 and multiplied in the monolayer were used for the production of transplantable cartilage tissue.

As described in Example 3, the chondrocytes multiplied in the monolayer were transferred into a special cell culture vessel which prevented sticking of the chondrocytes, so that, after a few days, aggregates or what are known as spheroids were formed. The spheroids were cultivated over a period of at least 1-2 weeks and formed a cartilage-like extracellular matrix (spheroid culture).

The marker for cartilage cell purity revealed the content of cartilage cells in the spheroid culture. In order to determine the cartilage cell purity in the spheroid culture, the total RNA of part of the chondrocytes cultivated in spheroids was isolated by means of conventional molecular biology techniques and was transcribed into cDNA by means of reverse transcriptase. The expression of at least one reference gene (above, Table 2) and of the identity marker "NRN1" was determined by means of standard polymerase chain reaction (PCR). The expression of "NR1" was set in relation to the expression of the reference gene and thus gave a normalised gene expression value for the purity marker "NRN1". If the expression of "NRN1" exceeds the previously defined threshold value for the purity, for example 1.0, this shows that chondrocytes of sufficient quality (purity) for transplantation of the cartilage tissue were present in the spheroid. If the threshold value for the purity is undershot, chondrocytes of insufficient quality (purity) are present in the spheroid for transplantation of the cartilage tissue. This cartilage tissue (chondrocytes of sufficient quality (purity) and cartilage-like extracellular matrix) is suitable, after introduction into the cartilage defect of the patient to be treated, for constructing a replacement cartilage tissue, which fills the defect and performs the function of the natural cartilage tissue. Cartilage tissue of insufficient quality (identity in the spheroid culture) is not suitable for constructing replacement cartilage tissue and was discarded.

EXAMPLE 6

Production of cartilage tissue to be transported by means of cartilage cells in spheroid culture and defined cellular impurities.

The cartilage cells isolated in Example 3 and multiplied in the monolayer were used for the production of transplantable cartilage tissue.

As described in Example 3, spheroids were formed and cultivated over a period of at least 1-2 weeks in order to form a cartilage-like extracellular matrix (spheroid culture). The marker for cartilage cell impurity indicates the content of cellular impurities with synovial cells, bone cells and/or fat cells in the spheroid culture. In order to determine cellular impurities of the cartilage cells in spheroid culture, the total RNA of part of the chondrocytes cultivated in the spheroids was isolated by means of conventional molecular biology techniques and was transcribed into cDNA by means of reverse transcriptase. The expression of at least one reference gene (above, Table 2) and of the impurity marker "EBF3" was determined by means of standard polymerase chain reaction (PCR). The expression of "EBF3" was set in relation to the expression of the reference gene and thus gives a normalised gene expression value for the impurity marker "EBF3". If the expression of "EBF3" undershot the previously defined threshold value for the impurity, for example 0.8, this indicated that there were no excessive cellular impurities by synoviocytes in the spheroid for transplantation of the cartilage tissue. If the threshold value for the impurity was exceeded, chondrocytes of insufficient quality (impurity) in the spheroid for transplantation of the cartilage tissue were present.

This cartilage tissue (chondrocytes of sufficient quality (impurity) and cartilage-like extracellular matrix) was suitable, after introduction into the cartilage defect of the patient to be treated, for building a replacement cartilage tissue, which filled the defect and performed the function of the natural cartilage tissue. Cartilage tissue of insufficient quality (increased content of cellular impurities) was not suitable for building replacement cartilage tissue and was discarded.

EXAMPLE 7

Production of cartilage tissue to be transplanted by means of cartilage cells in spheroid culture of defined potential.

The cartilage cells isolated in Example 3 and multiplied in the monolayer were used for the production of transplantable cartilage tissue.

As described in Example 3, spheroids were formed and cultivated over a period of at least 1-2 weeks in order to form a cartilage-like extracellular matrix (spheroid culture). The marker for cartilage cell potential revealed that cartilage cells in the spheroid culture had the capability of forming a cartilage-like extracellular matrix. In order to determine the potential of cartilage cells in spheroid culture, the total RNA of part of the chondrocytes cultivated in the spheroids was isolated by means of conventional molecular biology techniques and was transcribed into cDNA by means of reverse transcriptase. The expression of at least one reference gene and of the potential marker "Aggrecan" was determined by means of standard polymerase chain reaction (PCR). The expression of "Aggrecan" was set in relation to the expression of the reference gene and thus gave a normalised gene expression value for the impurity marker "Aggrecan". If the expression of "Aggrecan" exceeded the previously defined threshold value for the potential, for example 0.1, this indicated that chondrocytes of sufficient quality (potential) were present in the spheroid for transplantation of the cartilage tissue. If the threshold value for the potential was undershot, chondrocytes of insufficient quality (insufficient potential) were present in the spheroid for transplantation of the cartilage tissue.

This cartilage tissue (chondrocytes of sufficient quality (potential) and cartilage-like extracellular matrix) was suitable, after introduction into the cartilage defect of the patient to be treated, for building a replacement cartilage tissue, which filled the defect and performed the function of the natural cartilage tissue. Cartilage tissue of insufficient quality (potential) was not suitable for building replacement cartilage tissue and was discarded.

EXAMPLE 8

Production of cartilage tissue to be transplanted by means of cartilage cells of defined quality.

The cartilage cells isolated in Example 3 and multiplied in the monolayer were used for the production of transplantable cartilage tissue.

As described in Example 3, spheroids were formed and cultivated over a period of at least 1-2 weeks in order to form a cartilage-like extracellular matrix (spheroid culture).

In order to detect high-quality spheroid cultures for transplantation and regeneration of articular cartilage defects, as described in Example 3, the identity was determined by means of the identity marker "KAL1" and by means of the identity marker "CRTAC1", as described in Example 4. In addition, the purity marker "NRN1" was determined, as described in Example 5, and the purity marker "EBF3" was determined, as described in Example 6. The potential marker "Aggrecan" was also determined, as described in Example 7. The cartilage tissue (chondrocytes of sufficient quality (identity in the monolayer culture and/or in the spheroid culture, sufficient purity and/or acceptable degree of cellular impurities and sufficient potential of forming a cartilage-like extracellular matrix) and cartilage-like extracellular matrix) was suitable, after introduction into the cartilage defect of the patient to be treated, for building a replacement cartilage tissue which filled the defect and performed the function of the natural cartilage tissue. Cartilage tissue of insufficient quality (no proven identity in the monolayer culture and/or in the spheroid culture, insufficient purity and/or insufficient degree of cellular impurities and insufficient potential to form cartilage-like extracellular matrix) was not suitable for building replacement cartilage tissue and was discarded.

EXAMPLE 9

The procedure described here in Example 8 was applied retrospectively to cartilage tissue to be transplanted from 20 patients, wherein cartilage tissue for regeneration of articular cartilage damage was used. The ability of the transplanted cartilage tissue to build replacement cartilage tissue was assessed clinically on the basis of an established cartilage repair score (KOOS—Knee injury and Osteoarthritis Outcome Score: Roos E M & Lohmander L S, Health and Quality of Life Outcomes 2003, 1:64), that is to say the clinical success of the treatment. To this end, the KOOS of each patient was determined by means of a patient questionnaire prior to the treatment with the cartilage tissue to be transplanted (base value). A year after the treatment with the cartilage tissue to be transplanted, the KOOS of each patient was determined again by means of patient questionnaire (1 year follow-up value). The clinical or therapeutic success of the treatment was confirmed if the difference (KOOS delta) between 1 year follow-up value and base value was at least 8 points (Roos E M & Lohmander L S, Health and Quality of Life Outcomes 2003, 1:64). If the difference (KOOS delta) between 1 year follow-up value and base value was less than 8 points, there was no clinical improvement as a result of the treatment, i.e. the therapy was considered to be unsuccessful.

It was found that in the transplantable cartilage tissue from 4 of the 20 patients (5697-1607, 5862-1311, 6070-2413, 6988-2423), the potential marker "Aggrecan" was below the defined limit value, whereas the identity of the cartilage cells could be determined on the basis of the identity markers "KAL1" and "CRTAC1". The expression values were above the defined limit values. The purity of the cartilage tissue to be transplanted could also be determined on the basis of the impurity marker "EBF3" and was confirmed; here, expression values were below the defined limit values. These 4 cartilage tissues to be transplanted therefore demonstrated insufficient quality for building replacement cartilage tissue and were discarded. This corresponded to a reject rate of 20% (4 of 20 cartilage tissues to be transplanted).

It was found that in the transplantable cartilage tissue from 16 of the 20 patients (6266-2601, 6658-2420, 7494-2284, 8528-2286, 9070-2709, 9110-2294, 5669-2263, 9110-2294, 6094-1312, 6340-2277, 6611-2418, 8315-2434, 8916-2440, 8931-126, 8948-2706, 8966-2441), the potential marker "Aggrecan" was also above the defined limit value, and the identity of the cartilage cells could be determined on the basis of the identity markers "KAL1" and "CRTAC1". The expression values were also above the defined limit values. The purity of the cartilage tissue to be transplanted could also be determined on the basis of the impurity marker "EBF3" and was confirmed; here, the expression values were below the defined limit values. These 16 cartilage tissues to be transplanted therefore demonstrated sufficient 8916-2440, 8931-1126, 8948-2706, 8966-2441) in whom a transplantable cartilage tissue of sufficient quality had been determined, there was a clinical improvement as a result of the treatment. The difference between the KOOS 1 year follow-up value and the KOOS base value was wat least 8 points, and the therapy consequently was successful.

TABLE 4

| | | | Quality markers for identity, purity/impurity and potential of 20 patients with known clinical treatment result (KOOS delta) | | | |
| --- | --- | --- | --- | --- | --- | --- |
| Patient - Indentifier | KOOS overall delta 1 year follow-up | KAL1 mRNA levels ML (T/R) [acceptance limit >1.0] | CRTAC1 mRNA levels (T/R) [acceptance limit >0.03] | EBF3 mRNA levels (T/R) [acceptance limit ≤0.4] | ACAN mRNA levels (T/R) [acceptance limit ≥0.29] | Quality Passed (yes/no) |
| 5697 - 1607 | −16.91 | n.d. | 2.63 | 0.106 | 0.2194 | No |
| 5862 - 1311 | 6.93 | n.d. | 1.997 | 0.0252 | 0.1909 | No |
| 6070 - 2413 | −27.89 | n.d. | 2.105 | 0.0321 | 0.201 | No |
| 6266 - 2601 | 23.265 | 15.07 | 1.02 | 0.0678 | 0.349 | Yes |
| 6658 - 2420 | 44.790 | 13.8 | 0.925 | 0.0371 | 0.8073 | Yes |
| 6988 - 2423 | 1.011 | 23.67 | 3.069 | 0.046 | 0.2427 | No |
| 7494 - 2284 | 16.63 | 13.7 | 2.773 | 0.2085 | 0.7286 | Yes |
| 8528 - 2286 | 55.31 | 98.42 | 2.071 | 0.0927 | 1.392 | Yes |
| 9070 - 2709 | 32.59 | 22.8 | 1.547 | 0.0404 | 0.5935 | Yes |
| 9110 - 2294 | 19.17 | 152.6 | 0.501 | 0.0706 | 2.221 | Yes |
| 5669 - 2263 | 20.51 | 12.05 | 2.576 | 0.0669 | 1.12 | Yes |
| 9110 - 2294 | 19.17 | 152.6 | 0.501 | 0.0706 | 2.221 | Yes |
| 6094 - 1312 | 14.00 | 25.97 | 2.537 | 0.0761 | 0.439 | Yes |
| 6340 - 2277 | 15.11 | 16.17 | 0.439 | 0.0459 | 0.2942 | Yes |
| 6611 - 2418 | 17.96 | 40.96 | 0.541 | 0.1905 | 0.9808 | Yes |
| 8315 - 2434 | 41.83 | 30.29 | 0.174 | 0.2405 | 2.628 | Yes |
| 8916 - 2440 | 25.47 | 19.51 | 1.513 | 0.1495 | 1.613 | Yes |
| 8931 - 1126 | 42.23 | 2.02 | 1.637 | 0.123 | 0.4226 | Yes |
| 8948 - 2706 | 42.15 | 39.52 | 3.028 | 0.1408 | 0.9095 | Yes |
| 8966 - 2441 | 9.48 | 30.05 | 0.2841 | 0.0482 | 0.5464 | Yes |

KOOS: Knee injury and Osteoarthritis Outcome Score.
n.d. = not determined.

quality for building replacement cartilage tissue and were used for transplantation. This corresponded to a success rate of 80% (16 of 20 cartilage tissues to be transplanted).

The transplantable cartilage tissue of 4 of the 20 patients (5697-1607, 5862-1311, 6070-2413, 6988-2423) thus demonstrated a cartilage tissue of insufficient quality (no proven identity in the monolayer structure and/or in the spheroid structure, insufficient purity and/or insufficient degree of cellular impurities and insufficient potential to form cartilage-like extracellular matrix), whereas the transplantable bone tissue from 16 of the 20 patients (6266-2601, 6658-2420, 7494-2284, 8528-2286, 9070-2709, 9110-2294, 5669-2263, 9110-2294, 6094-1312, 6340-2277, 6611-2418, 8315-2434, 8916-2440, 8931-1126, 8948-2706, 8966-2441) had a cartilage tissue of sufficient quality (identity in the monolayer structure and/or in the spheroid structure, sufficient purity and/or sufficient degree of cellular impurities and sufficient potential to form cartilage-like extracellular matrix).

With regard to the clinical or therapeutic success of the treatment, it was found (see Table 4) that in those 4 of the 20 patients (5697-1607, 5862-1311, 6070-2413, 6988-2423) in whom a transplantable cartilage tissue of insufficient quality had been determined retrospectively, there was no clinical improvement as a result of the treatment. The difference between the KOOS 1 year follow-up value and the KOOS base value was less than 8 points, and the therapy consequently was unsuccessful. By contrast, it was found that in those 16 of the 20 patients (6266-2601, 6658-2420, 7494-2284, 8528-2286, 9070-2709, 9110-2294, 5669-2263, 9110-2294, 6094-1312, 6340-2277, 6611-2418, 8315-2434,

The invention claimed is:

1. A method for selecting chondrocytes for production of transplantable cartilage tissue, the method comprising:
   multiplying the chondrocytes in a monolayer culture;
   determining gene expression levels of anosmin 1 (KAL1) in the multiplied chondrocytes in the monolayer culture;
   selecting multiplied chondrocytes that express KAL1;
   aggregating the selected multiplied chondrocytes to form spheroids;
   determining gene expression levels of cartilage acidic protein 1 (CRTAC1) and early B-cell factor 3 (EBF3), and at least one of neuritin 1 (NRN1) and aggrecan (ACAN) in the spheroids; and
   selecting spheroids that express CRTAC1 and at least one of NRN1 and ACAN but have expression levels of EBF3 below a predetermined threshold value for the production of the transplantable cartilage tissue.

2. The method for selecting chondrocytes according to claim 1, wherein the gene expression level of KAL1 is compared to a gene expression level of a reference gene R in the multiplied chondrocytes, the gene expression levels of CRTAC1, EBF3, and at least one of NRN1 and ACAN are compared to a gene expression level of the reference gene R in the spheroids, the multiplied chondrocytes and the spheroids are selected if ratios of the gene expression levels of the genes to the reference gene R are CRTAC1/R≥0.003; NRN1/R≥0.1; KAL1/R>1.0; EBF3/R≤0.4; and ACAN/R≥0.29, the multiplying step is carried out at 37° C., and
   R is selected from the group consisting of beta-2-microglobulin (B2M) and topoisomerase I (TOP1).

3. The method for selecting chondrocytes according to claim 2, wherein the ratios of the gene expression levels of the genes to the reference gene R are CRTAC1/R≥0.006; NRN1/R≥0.2; KAL1/R≥2.0; EBF3/R≤0.3; and ACAN/R≥0.39.

4. The method for selecting chondrocytes according to claim 1, wherein a proportion of synoviocytes in the chondrocytes after multiplication or in the obtained spheroids in relation to the total cell number is less than or equal to 9%.

5. A method for selecting chondrocytes for the production of transplantable cartilage tissue, the method comprising:

multiplying the chondrocytes in a monolayer culture;

determining gene expression levels of KAL1 in the multiplied chondrocytes;

selecting multiplied chondrocytes that express KAL1;

aggregating the selected multiplied chondrocytes to form spheroids;

determining gene expression levels of cartilage acidic protein 1 (CRTAC1), neuritin 1 (NRN1), aggrecan (ACAN), and early B-cell factor 3 (EBF3) in the spheroids; and selecting spheroids that express CRTAC1, NRN1, and ACAN but have expression levels of EBF3 below a predetermined threshold value for the production of the transplantable cartilage tissue.

6. The method for selecting chondrocytes according to claim 5, wherein the gene expression level of KAL1 is compared to a gene expression level of a reference gene R in the multiplied chondrocytes, the gene expression levels of CRTAC1, NRN1, ACAN, and EBF3 are compared to a gene expression level of the reference gene R in the spheroids, the multiplied chondrocytes and the spheroids are selected if ratios of the gene expression levels of the genes to a reference gene R are CRTAC1/R≥0.003; NRN1/R≥0.1; KAL1/R>1.0; EBF3/R≤0.4; and ACAN/R≥0.29, the multiplying step is carried out at 37° C., and R is selected from the group consisting of B2M and TOP1.

7. The method for selecting chondrocytes according to claim 6, wherein the ratios of the gene expression levels of the genes to the reference gene R are CRTAC1/R≥0.006; NRN1/R≥0.2; KAL1/R≥2.0; EBF3/R≤0.3; and ACAN/R≥0.39, wherein R for KAL1 is a reference gene of the multiplied chondrocytes and R for CRTAC1, NRN1, ACAN, and EBF3 is a reference gene of the spheroids, and wherein R is selected from the group consisting of B2M and TOP1.

8. A method for selecting chondrocytes for the production of transplantable cartilage tissue, the method comprising:

multiplying the chondrocytes in a monolayer culture;

determining gene expression levels of KAL1 in the multiplied chondrocytes;

selecting multiplied chondrocytes that express KAL1; and aggregating the selected multiplied chondrocytes to form spheroids;

determining gene expression levels of cartilage acidic protein 1 (CRTAC1), aggrecan (ACAN), and early B-cell factor 3 (EBF3) in the spheroids; and selecting spheroids that express CRTAC1 and ACAN but have expression levels of EBF3 below a predetermined threshold value for the production of the transplantable cartilage tissue.

* * * * *